(12) United States Patent
Paul, Jr.

(10) Patent No.: US 8,192,479 B2
(45) Date of Patent: Jun. 5, 2012

(54) METHOD AND DEVICE FOR VASCULAR THERAPY

(75) Inventor: Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 493 days.

(21) Appl. No.: 12/324,484

(22) Filed: Nov. 26, 2008

(65) Prior Publication Data

US 2009/0143851 A1    Jun. 4, 2009

Related U.S. Application Data

(60) Provisional application No. 60/991,291, filed on Nov. 30, 2007.

(51) Int. Cl.
*A61F 2/06* (2006.01)
*A61F 2/01* (2006.01)
*A61M 29/00* (2006.01)

(52) U.S. Cl. ............ 623/1.11; 623/1.15; 623/1.13; 606/198; 606/200

(58) Field of Classification Search .......... 623/1.11, 623/1.15, 1.18, 1.2, 1.3, 1.23, 1.13; 606/198, 606/200, 153
See application file for complete search history.

(56) References Cited

U.S. PATENT DOCUMENTS

| | | | |
|---|---|---|---|
| 4,997,435 A | 3/1991 | Demeter | 606/127 |
| 5,234,458 A | 8/1993 | Metais | 606/200 |
| 5,368,566 A | 11/1994 | Crocker | 604/101 |
| 5,456,667 A * | 10/1995 | Ham et al. | 604/107 |
| 5,522,790 A | 6/1996 | Moll et al. | 600/204 |
| 5,571,086 A | 11/1996 | Kaplan et al. | 604/96 |
| 5,597,378 A | 1/1997 | Jervis | 606/78 |
| 5,713,907 A | 2/1998 | Hogendijk et al. | 606/108 |
| 5,733,325 A * | 3/1998 | Robinson et al. | 623/1.11 |
| 5,795,322 A * | 8/1998 | Boudewijn | 604/22 |
| 5,904,670 A | 5/1999 | Schreiner | 604/280 |
| 6,013,019 A | 1/2000 | Fischell et al. | 600/3 |

(Continued)

FOREIGN PATENT DOCUMENTS

WO     WO 95/31945     11/1995

OTHER PUBLICATIONS

"Shape Memory Alloys," Scientific American, 281:74-82 (Nov. 1979).

(Continued)

*Primary Examiner* — Amy Lang
(74) *Attorney, Agent, or Firm* — Brinks Hofer Gilson & Lione

(57) ABSTRACT

Medical devices, as well as methods of treatment and manufacturing such devices, are provided for applying vascular therapy locally within the body vessel. The medical devices include an expandable tubular frame and a sleeve. The medical devices can be used for local delivery of a therapeutic agent within a body vessel or a tamponade for a lacerated body vessel, while simultaneously allowing perfusion of fluid or blood flow distal of the implanted medical device. The tubular frame of the medical device can have a middle region with a plurality of members. The members can expand radially outward away from a longitudinal axis of the tubular frame, which can urge the sleeve to contact the wall of the body vessel. In the expanded configuration, a portion of the device allows fluid flow to continue while the sleeve is against the body vessel wall.

18 Claims, 3 Drawing Sheets

U.S. PATENT DOCUMENTS

| | | | | |
|---|---|---|---|---|
| 6,159,139 | A | 12/2000 | Chiu | 600/3 |
| 6,162,237 | A | 12/2000 | Chan | 606/198 |
| 6,206,931 | B1 | 3/2001 | Cook et al. | 623/23.75 |
| 6,217,585 | B1 | 4/2001 | Houser et al. | 606/108 |
| 6,231,561 | B1 | 5/2001 | Frazier et al. | 604/500 |
| 6,409,752 | B1 | 6/2002 | Boatman et al. | 623/1.15 |
| 6,500,182 | B2 | 12/2002 | Foster | 606/127 |
| 6,676,692 | B2 | 1/2004 | Rabkin et al. | 623/1.11 |
| 6,893,431 | B2 | 5/2005 | Naimark et al. | 604/891.1 |
| 7,037,321 | B2 | 5/2006 | Sachdeva et al. | 606/200 |
| 7,060,091 | B2 * | 6/2006 | Killion et al. | 623/1.15 |
| 7,094,765 | B1 | 8/2006 | Iversen et al. | 514/44 |
| 7,128,073 | B1 | 10/2006 | Van der Burg et al. | 128/887 |
| 7,160,592 | B2 | 1/2007 | Rypacek et al. | 428/36.9 |
| 7,179,275 | B2 | 2/2007 | McGuckin, Jr. et al. | 606/200 |
| 7,338,512 | B2 | 3/2008 | McGuckin, Jr. et al. | 606/200 |
| 7,871,440 | B2 * | 1/2011 | Schwartz et al. | 623/14.12 |
| 7,914,567 | B2 * | 3/2011 | Pavcnik et al. | 623/1.13 |
| 2003/0023265 | A1 * | 1/2003 | Forber | 606/200 |
| 2003/0100886 | A1 | 5/2003 | Segal et al. | 604/509 |
| 2003/0153870 | A1 | 8/2003 | Meyer et al. | 604/96.01 |
| 2003/0204168 | A1 * | 10/2003 | Bosma et al. | 604/103.02 |
| 2004/0024448 | A1 | 2/2004 | Chang et al. | 623/1.42 |
| 2004/0122468 | A1 * | 6/2004 | Yodfat et al. | 606/200 |
| 2004/0236186 | A1 | 11/2004 | Chu | 600/215 |
| 2005/0113902 | A1 * | 5/2005 | Geiser et al. | 623/1.11 |
| 2006/0041271 | A1 * | 2/2006 | Bosma et al. | 606/200 |
| 2006/0074480 | A1 * | 4/2006 | Bales et al. | 623/1.15 |
| 2006/0149312 | A1 | 7/2006 | Arguello et al. | 606/200 |
| 2006/0269587 | A1 | 11/2006 | Iversen et al. | 424/426 |
| 2007/0073381 | A1 * | 3/2007 | Jones | 623/1.15 |
| 2007/0088383 | A1 * | 4/2007 | Pal et al. | 606/200 |
| 2007/0148243 | A1 * | 6/2007 | Bates | 424/484 |
| 2008/0058763 | A1 | 3/2008 | Boland et al. | 604/522 |
| 2009/0030499 | A1 * | 1/2009 | Bebb et al. | 623/1.13 |

OTHER PUBLICATIONS

Dougal et al., "Stent Design: Implications for Restenosis," Rev. Cardiovasc Med. 3 (suppl. 5), S16-S22 (2002).

* cited by examiner

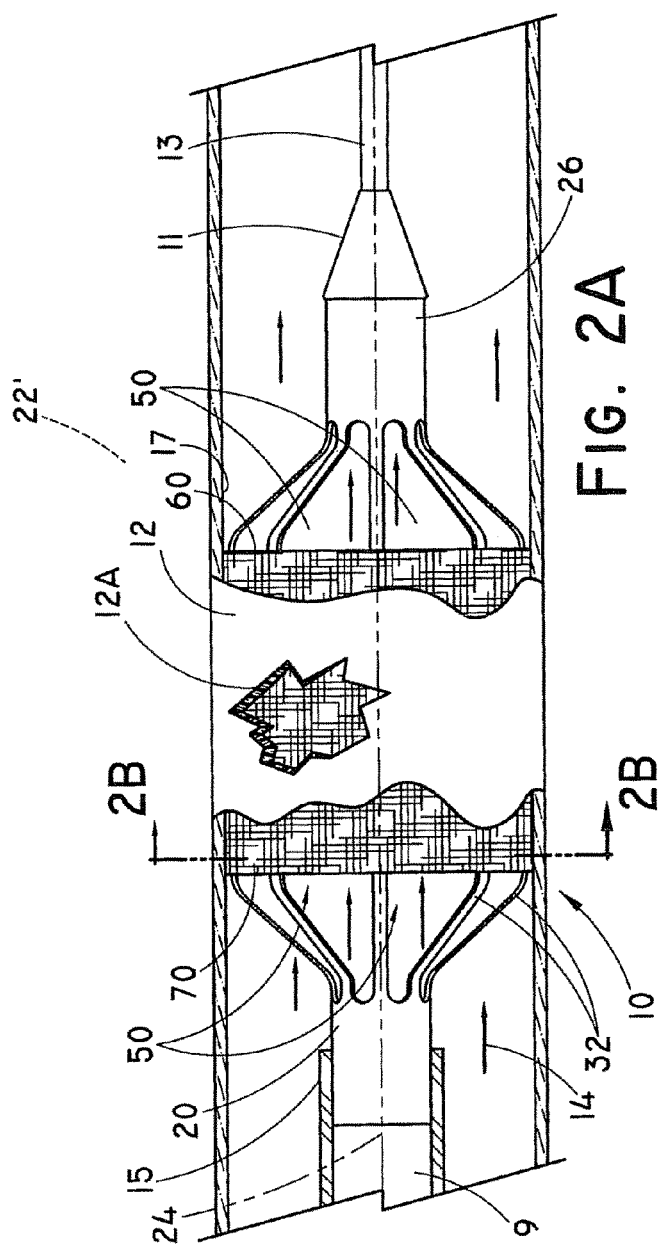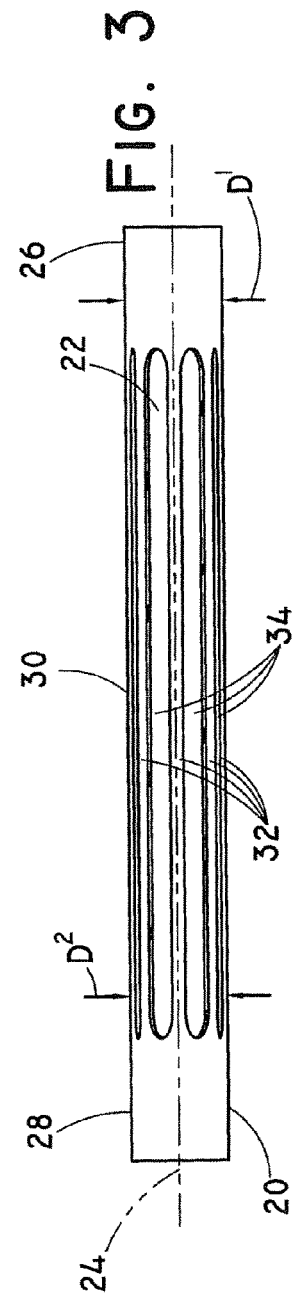

METHOD AND DEVICE FOR VASCULAR THERAPY

CROSS-REFERENCE TO RELATED PATENT APPLICATION

This application claims the benefit of the filing date under 35 U.S.C. §119(e) of U.S. Provisional Patent Application No. 60/991,291, filed Nov. 30, 2007, which is hereby incorporated by reference.

TECHNICAL FIELD

This invention relates to the field of medical devices and, more particularly, to a medical device, and methods of treatment and manufacturing such device, for applying vascular therapy locally within a body vessel.

BACKGROUND

Vascular therapy can encompass many medical treatments to the vascular system. One example is the general systemic administration of a therapeutic agent within a body vessel. Although many medical conditions are satisfactorily treated by the general systemic administration of the therapeutic agent, the treatment of many conditions require delivery of the therapeutic agent locally within a body vessel. More specifically, delivery of the therapeutic agent is to only a selected portion of internal body tissue, without delivering the therapeutic agent to surrounding tissue or requiring additional systemic delivery of the therapeutic agent. A systemically administered therapeutic agent may be absorbed not only by the tissues at the target site, but by other areas of the body. As such, one drawback associated with the systemic administration of therapeutic agents is that areas of the body not needing treatment are also affected.

Medical delivery catheters provide a minimally invasive means for delivering therapeutic agents to internal body tissue. To provide site-specific localized treatment, balloon catheters may be used to deliver the therapeutic agent exclusively to the target site within a body vessel. One example of a condition that is beneficially treated by local administration of the therapeutic agent with a balloon catheter is the delivery of the therapeutic agent in combination with percutaneous transluminal coronary angioplasty (PTCA). PTCA is a technique used to dilate stenotic portions of blood vessels. During PTCA, a catheter balloon is positioned at a blocked lumen or target site, and the balloon is inflated to cause dilation of the lumen. The balloon is deflated and the catheter is then removed from the target site and from the patient's lumen thereby to allow blood to flow freely through the unrestricted lumen.

Although PTCA and related procedures aid in alleviating intraluminal constrictions, such constrictions or blockages may reoccur in many cases. The cause of these recurring obstructions, termed restenosis, may be due to the body responding to the surgical procedure. Restenosis of the artery commonly develops over several months after the procedure, which may require another angioplasty procedure or a surgical by-pass operation. Proliferation and migration of smooth muscle cells (SMC) from the media layer of the lumen to the intima cause an excessive production of extra cellular matrices (ECM), which is believed to be one of the leading contributors to the development of restenosis. The extensive thickening of tissues narrows the lumen of the blood vessel, constricting or blocking the blood flow through the vessel. Therapeutic agents selected to limit or prevent restenosis may be locally delivered with PTCA from a catheter and/or by placement of a stent configured to release the therapeutic agent after the PTCA procedure. Catheter balloons may be used in combination with stents, synthetic vascular grafts or drug therapies during the PTCA procedure to reduce or eliminate the incidence of restenosis. Yet, some catheter balloons may occlude or block blood flow distal to the treatment site. Some perfusion balloon catheters only allow a small percentage of perfusion. For example, a balloon catheter sized for a 6 mm body vessel may only provide a 1 mm passageway.

Another type of vascular therapy is gaining hemostasis with a lacerated hole in the body vessel. During emergency procedures, quick hemostasis is desirable to prevent any more blood from leaving the body. Conventional methods of promoting hemostasis is by applying pressure over the blood vessel manually and then by applying a pressure bandage, compressive weight, or clamp device, while applying a therapeutic agent. Some devices can be implanted within the body vessel to block the lacerated hole. However, these devices are typically left permanently within the body vessel, which are likely to promote a risk of closure or acutely clot formation in only a few years, and difficult to remove otherwise.

In view of current devices and methods, there is a need for a medical device for applying vascular therapy locally within a body vessel while allowing fluid flow to areas distal to the treatment site.

SUMMARY

Accordingly, a medical device and method for applying vascular therapy locally within a body vessel is provided. The medical device is an alternative therapy to intravascular drug treatment using balloon catheters or stents. The medical device can also be an alternative therapy to apply hemostasis to a lacerated hole. The medical device can be left in the body vessel for between a few minutes to permit an effective delivery of the therapeutic agent to a few hours or days to permit effective hemostasis and/or remodeling.

The medical device includes a tubular frame and a sleeve and may also include a therapeutic agent. The tubular frame defines a lumen about a longitudinal axis and includes a distal end, a proximal end, and a middle region. The middle region of the tubular frame includes a plurality of members defining a series of slots therebetween. The slots may be oriented substantially parallel to the longitudinal axis and/or one another, or may be circumferentially spaced substantially equal around the middle region of the tubular frame, or both. The tubular frame may be, self-expanding and comprise a shape memory alloy.

The middle region of the tubular frame is movable between a compressed configuration and an expanded configuration. The members in the compressed configuration are configured to lie in immediate contiguous proximity to each other and/or substantially flat to decrease the profile of the medical device for delivery to the treatment site. In the expanded configuration are configured to be displaced radially outward from the longitudinal axis to close proximity to the body vessel to form interstices between the members. In the expanded configuration and the compressed configuration, the distal end and the proximal end of the tubular frame can have a similar diameter. The middle region of the tubular frame can have a first diameter in the compressed configuration and a second diameter in the expanded configuration that is greater than the first diameter, where the first diameter of the middle region is substantially identical to the diameter of the proximal and distal ends of the tubular frame.

The sleeve encompasses a portion of the middle region of the tubular frame. The sleeve may be maintained in contact with at least a portion of the members. The sleeve may be elastic and may exert a radially compressing restoring force on the middle region of the tubular frame. The sleeve can provide a media for a therapeutic agent. The therapeutic agent can be configured to be delivered when the sleeve is in contact with the wall of the body vessel. In another embodiment, the sleeve can also comprise a remodelable material, such as foamed extracellular matrix (ECM), where the sleeve can be applied to a lacerated hole to promote hemostasis and/or remodeling.

In another embodiment, each member can have two bends and a contacting portion therebetween while in the expanded configuration, where the contacting portion is configured to substantially align with the body vessel wall. Preferably, the alignment of the contacting portion increases the contacting area axially along the treatment site to permit delivery vascular therapy more effectively.

In another embodiment, the tubular frame is formed from a shape memory alloy. In this instance, the members and the middle region of the tubular frame are biased toward the expanded configuration to have a maximum radial force at 37 degrees C. The middle region of the tubular frame, consequently, can be compressed by disposing a sheath about the expanded middle region to urge the members to the compressed configuration during delivery, and can expanded by removing the sheath from the middle region during deployment. Optionally, a means for translating the distal end of the tubular frame along the longitudinal axis relative to the proximal end of the tubular frame to urge the members to move the members between the compressed configuration and the expanded configuration can be provided.

In another embodiment, a system is provided including the medical device and a catheter shaft attached to the medical device. Optionally, a sheath can be disposed radially outward from the catheter shaft and slidably engaged thereto. The sheath is movable and sized to compress the medical device. The system may also include a dilator to improve the transition from the guide wire to the medical device when being delivered.

One feature of the present invention is that the medical device in the expanded configuration has a portion or a sleeve positioned against the wall of the body vessel in order to treat the body vessel. Another feature is that the medical device in the expanded configuration has adequate interstices in another portion to allow fluid flow to the areas distal of the treatment site. This is especially critical when the distal areas are organs, such as the brain, heart or kidneys. When the sleeve includes a therapeutic agent, it is desirable that the therapeutic agent be applied to the treatment site in the body vessel wall, while maintaining fluid perfusion distal to the medical device, in order to avoid significantly affecting nontreatment sites elsewhere.

The above, as well as other advantages of the present invention, will become readily apparent to those skilled in the art from the following detailed description of a preferred embodiment when considered in the light of the accompanying drawings.

BRIEF DESCRIPTION OF THE DRAWINGS

FIG. 2A is a side view of a medical device within a body vessel.

FIG. 3 is a side view of a tubular frame of a medical device in the compressed configuration.

DETAILED DESCRIPTION OF THE DRAWINGS AND THE PRESENTLY PREFERRED EMBODIMENTS

Figure 1:
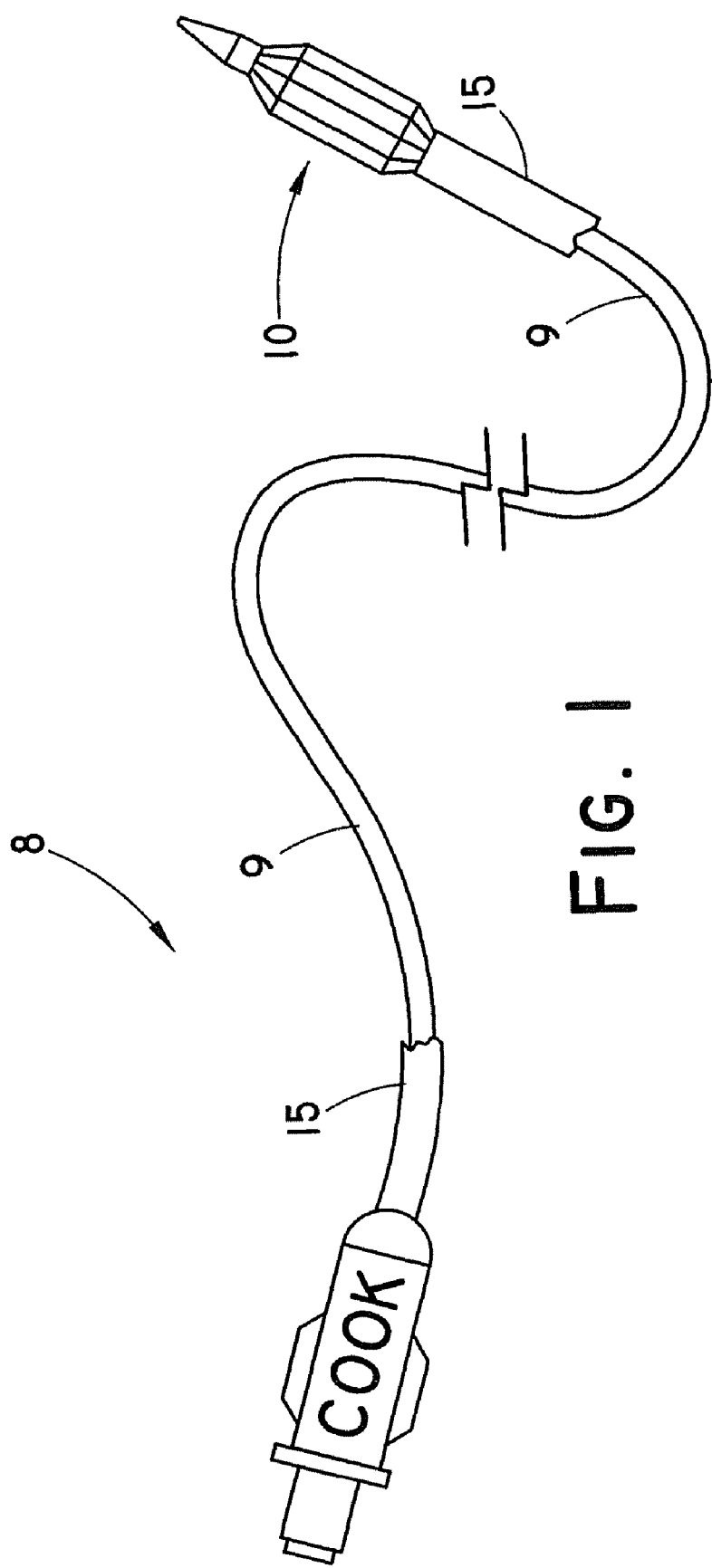
FIG. 1 is a perspective view of a system comprising a medical device and a catheter shaft.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "medical device" is utilized herein to represent a combination of components and individual components, regardless of whether the components are combined with other components. In addition, it is noted that the term "method(s)" or "step(s)" is utilized herein to represent a combination of steps and individual steps, regardless of whether the steps are combined with other steps.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue. The term "substantially" is further utilized herein to represent a minimum degree to which a quantitative representation must vary from a stated reference to yield the recited functionality of the subject matter at issue.

In the following discussion, the terms "proximal" and "distal" will be used to describe the opposing axial ends of the medical device, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient.

Provided are a perfusion medical device and system for applying vascular therapy locally within a body vessel. The medical device and method are alternative therapies to instravascular drug treatment using balloon catheters or stents. Moreover, the medical device can also be an alternative therapy to apply hemostasis and/or remodeling to a lacerated hole. The medical device can expand to an expanded configuration in order to have a portion or sleeve positioned at the body vessel wall, while simultaneously providing adequate interstices in another portion to allow fluid flow and perfusion to areas distal of the treatment site. This is especially critical when it is undesirable to block fluid or fluid or blood flow for an extended period of time to organs, such as the brain, heart or kidneys, while waiting for the therapy to be complete; for example, to allow the therapeutic agent to diffuse into the target tissue.

Figure 4A:
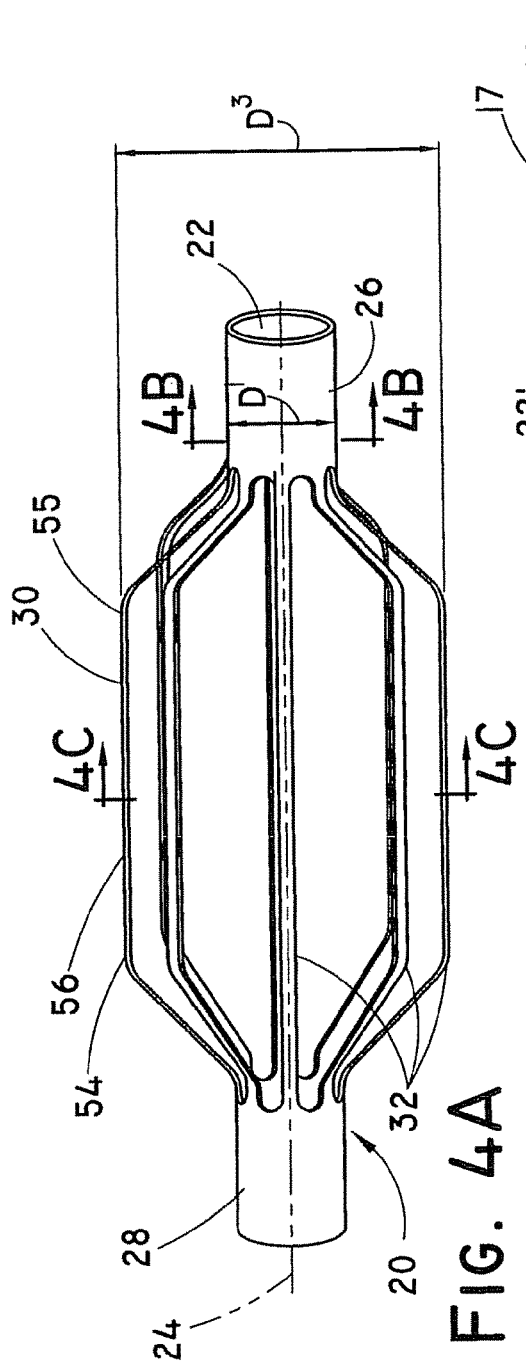
FIG. 4A is a perspective view of a medical device in the expanded configuration.

FIG. 1, a system 8 for applying vascular therapy locally within a body vessel. The system includes a medical device 10 and a catheter shaft 9. The catheter shaft 9 may be attached to a proximal end 28 of the tubular frame 20. In particular, FIGS. 3 and 4A depict a tubular frame 20 of the medical device 10 having defining a lumen 22 about a longitudinal axis 24. The tubular frame 20 has a distal end 26, the proximal end 28, and a middle region 30 disposed therebetween. The attachment between the catheter body 9 and the medical device 10 can be by any method known in the art, including welding, adhesive application or any suitable mechanical means. FIG. 2A illustrates that the system 8 can also include a dilator 11 which can be engaged with the distal end 26 of the tubular frame 20. The catheter shaft 9 and the dilator 11 can have a wire guide lumen for receiving a wire guide 13. A sheath 15 disposed radially outward of the catheter shaft 9 and slidably engaged with the catheter shaft 9 can also be provided, as shown in FIGS. 1 and 2A. The sheath 15 can protect the medical device 10 during delivery and/or urge the medical device 10 to be maintained in the compressed configuration during delivery.

Figure 2B:
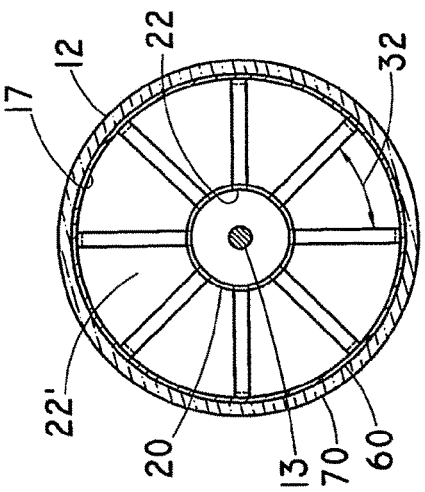
FIG. 2B is a cross-sectional view taken along line 2B-2B in FIG. 2A.

FIGS. 2A-2B show an illustrative medical device 10 according to one embodiment of the present invention implanted with a body vessel 12. FIG. 2A illustrates a partial cross-sectional view of the body vessel 12 and an exterior portion of the body vessel 12, where at the exterior portion the body 12 has a lacerated hole 12A. The lacerated hole 12A is for illustrated purposes for some forms of vascular therapy, and it is appreciated that the other forms of vascular therapy do not require a lacerated hole. Here, the medical device 10 is in an expanded configuration contacting a wall 17 of the body vessel 12. FIG. 2B is a cross sectional view taken along line 2B-2B in FIG. 2A. Although the cross-sectional view of the medical device 10 define a non-limiting periphery that is circular, various shapes such as elliptical or others appreciated by one of ordinary skill in the art is within the scope of the present application.

The medical device 10 includes the tubular frame 20 and a sleeve 60, and may further include a therapeutic agent 70. According to FIG. 3, the tubular frame 20 is shown in a compressed configuration configured for delivery into the body vessel, and according to FIGS. 2A and 4A, the tubular frame 20 is shown in the expanded configuration.

Figure 4C:
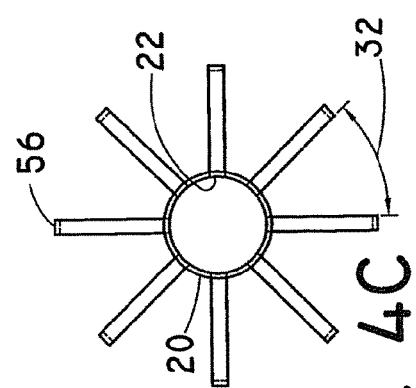
FIG. 4C is a cross-sectional view taken along line 4C-4C in FIG. 4A.
Figure 4B:
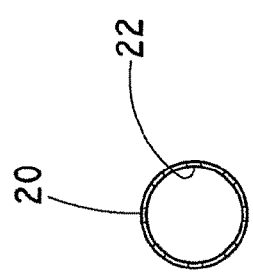
FIG. 4B is a cross-sectional view taken along line 4B-4B in FIG. 4A.

The tubular frame 20 can have a first diameter, noted as "D1" in FIGS. 3 and 4A, at the distal end 26 and the proximal end 28 in both the expanded configuration and the compressed configuration. FIG. 4B is a cross-sectional view taken along line 4B-4B in FIG. 4A depicting the preferable low profile of the tubular frame 20 of the medical device 10. The first diameter D1 of the proximal end 28 and the distal end 26 of the tubular frame 20 may be substantially the same. However, the diameter of proximal end 28 and the distal end 26 of the tubular frame 20 may also be different. That is, the diameter of the proximal end 28 may be less than or greater than the diameter of the distal end 26.

In FIG. 3, the middle region 30 of the tubular frame 20 includes a plurality of members 32. The members 32 define a series of slots 34 in between adjacent members. The series of slots 34 can be oriented substantially parallel to one another, circumferentially spaced equally around the middle region 30, or both. The diameter of the middle region 30 of the tubular frame 20 can be different depending on whether the tubular frame 20 is in the compressed configuration or in the expanded configuration. That is, the middle region 30 can have a first diameter, noted as "D2" in FIG. 3, in the compressed configuration and a second diameter, noted as "D3" in FIG. 4A, in the expanded configuration. The second diameter D3 is preferably sized to fit within the body vessel 12. FIG. 4C is a cross-sectional view taken along line 4C-4C in FIG. 4A depicting the members 32 without the sleeve 60. The second diameter D3 of the middle region 30 is greater than the first diameter D2 of the middle region 30. Preferably, the first diameter D2 of middle region 30 is the same or substantially the same as the diameter D1 of the tubular frame 20. However, the diameter D2 of middle region 30 may be different than the first diameter D1 of the tubular frame 20. In that case, the first diameter D2 of the middle region 30 may be less than or greater than the first diameter D1 of the tubular frame 20. In one example, the diameters D1, D2 are about 1 mm, and D3 can be about 4, 5, or 6 mm. The size of diameter D3 may also be about 4 mm to about 20 mm or more depending on the size of the body vessel, while diameters D1, D2 may be about 1 mm to about 5 mm. Although the Figures illustrate the medical device having a middle region that is substantially cylindrical, the middle region 30 may be suitably tapered to better match the shape of the body vessel.

The members 32 may be configured to be substantially straight and/or flat or in immediate contiguous proximity to each other without a substantial bent portion in the compressed configuration in order to make a more uniform profile during delivery, as shown in FIGS. 3 and 4B. In FIG. 4A, in the expanded configuration, the members 32 can have two vertices or bent portions 54, 55, a contacting portion 56 in between the vertices 54, 55, or both, which can contact with the body vessel 12. Portions between the bent portions 54, 55 and the respective proximal and distal ends 26, 28 are suitably angled in order to form the contacting portions 56 and the interstices 50 when in the expanded configuration. The contacting portion 56 of the members 32 is configured to substantially align with the body vessel wall 17 while the tubular frame 20 is in the expanded configuration. Accordingly, the members 32 and the contacting portion 56 can have a cylindrical shape or can be suitably tapered to match the tapering of a body vessel. Preferably, the contacting portion 56 of the members 32 can be substantially straight and/or parallel to increase the contact area between the contacting portion 56 of the members 32 and the wall 17 of the body vessel 12. This increased contact area can permit better engagement of the sleeve 60 with the body vessel wall 17 and to more effectively allow vascular therapy of the body vessel 12. In other examples, the members 32 in the expanded configuration are configured to form a balloon-like shape. The contacting portion 56 of the members 32 may also have a concave curvature between the vertices 54, 55. The number of members 32 can vary from 3, 4, 5, 6, 7, 8, 9, 10 or more depending on the desired support for the body vessel.

Referring to FIGS. 2A and 2B, the sleeve 60 can be shaped and sized to encompass the whole tubular frame 20. In particular, the sleeve 60 may also shaped and sized to encompass the middle region 30, or only a portion of the middle region 30. The sleeve 60 can be placed to surround the tubular frame 20 while the tubular frame 20 is in the compressed configuration or in the expanded configuration. Regardless, the tubular frame 20 can be maintained to contact with at least a portion of the members 32 in the compressed configuration and in the expanded configuration.

The attachment and placement of the sleeve 60 can allow sufficient fluid or blood flow 14 to areas distal to the medical device 10. Preferably, the sleeve 60 is positioned on the middle region 30, and is not in the area created by the transition between the diameters D1, D3 of the respective proximal and/or distal ends 28, 26 and the middle region 30. In such case, blood flow 14 can flow outside the proximal end 28 of the tubular frame 20, through the interstices 50 and the lumen 22' created by the middle portion 30 of the tubular frame 20 and sleeve 60 in the expanded configuration, and outside the distal end 26 of the tubular frame 20. Preferably, the blood flow 14 does not enter the contact area between the sleeve 60 and the wall 17 of the body vessel 12.

The sleeve 60 can be attached to the tubular frame 20 by, or the sleeve 60 can be free-standing or friction-fitted. If attached, the most common ways can be with an adhesive, with winding a filament (e.g., suture, etc.), or both. Moreover, the sleeve 60 can have a minimal thickness to minimize the profile of the medical device 10. In one non-limiting example the sleeve 60 has a thickness of about 0.5 mm (0.020 inches). In some examples, the sleeve 60 comprises a porous material, such as (PTFE). When the sleeve 60 comprises a minimally expandable material, the sleeve 60 is sized to fit the middle region 30 in the expanded configuration. As a result, when the middle region 30 is in the compressed configuration, portions of the sleeve 60 can be folded into the lumen 22 through the slots 34 in order to minimize the delivery profile.

In some examples, the sleeve 60 comprises a remodelable material. Remodelable material is capable of remodeling or promoting cell growth and/or promoting regrowth and healing of damaged or diseased tissue structures. The remodelable material can be extra cellular material (ECM), small intestine submucosa (SIS), remodelable or collagenous foam, foamed ECM, lyophilized SIS or vacuum pressed SIS. One non-limiting example of a suitable remodelable material is the SURGISIS® BIODESIGN™, commercially available from Cook Incorporated, Bloomington, Ind. Another suitable remodelable material is the graft prosthesis material described in U.S. Pat. No. 6,206,931 to Cook et al., incorporated herein by reference.

Yet, in another embodiment, the sleeve 60 is expandable. In one example, the sleeve 60 should has an elasticity capable of exerting a radially compressing restoring force on the tubular frame 20, or on the middle region 30 of the tubular frame 20, in the expanded configuration. In other words, the sleeve 60 may be biased toward the compressed configuration to hold and maintain contact with the middle region 30 of the tubular frame 20 in the compressed configuration or the expanded configuration. The sleeve 60 may include a material with a desired restoring force to maintain contact with the tubular frame. For example, the sleeve 60 may be formed from elastic or one or more polymers selected from the group consisting of a rubber or rubberized material, silicone, polyurethane, a thermoplastic elastomer, nylons or other polyamides, polyethylene terephthalate (PET), polyether block amides (PEBA), and mixtures of the foregoing. Other materials such as ethylene vinyl acetate, latexes, urethanes, polysiloxanes, styrene-ethylene/butylene-styrene block copolymers, silicone rubber, SILASTIC, aliphatic polyesters, and mixtures and copolymers may also be included in the sleeve 60.

The tubular frame 20 may be formed from any suitable material. Preferred materials include those materials that can provide the desired functional characteristics with respect to mechanical load bearing, biological compatibility, modulus of elasticity, radio-opacity, or other desired properties. For some embodiments, the materials used to form the tubular frames can comprise a material that exhibits excellent corrosion resistance. For some embodiments, the material can be selected to be sufficiently radiopaque and create minimal artifacts during magnetic resonance imaging techniques (MRI). In some embodiments, the tubular frame can comprise a metal, a metal alloy, a polymer, or any suitable combination thereof, for example as frame with multiple layers.

Preferably, the tubular frame 20 can be self-expanding comprising a material capable of significant recoverable strain to assume a low profile for delivery to a desired location within a body lumen. After release of the compressed frame, it is preferred that the frame be capable of radially expanding back to its original diameter or close to its original diameter. Accordingly, some embodiments provide a tubular frame 20 made from material with a low yield stress (to make the frame deformable at manageable balloon pressures), high elastic modulus (for minimal recoil), and is work hardened through expansion for high strength. Particularly the preferred materials for a self-expanding tubular frame 20 is shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for frames 20 or cannulas can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing tubular frames 20 can be obtained from, e.g., Memory Corp., Brookfield, Conn. One suitable material possessing desirable characteristics for self-expansion is Nitinol, a Nickel-Titanium alloy that can recover elastic deformations of up to 10 percent. This unusually large elastic range is commonly known as superelasticity.

When the tubular frame 20 is formed from superelastic nickel-titanium (NiTi) alloys, the self-expansion occurs when the stress of compression is removed. This allows the phase transformation from martensite back to austenite to occur, and as a result the tubular frame 20 expands. Materials having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When the tubular frames 20 are deformed while in the martensitic phase, the frames retain this deformation as long as the frames remain in the same phase, but revert to the original configuration when the frames are heated to a transition temperature, at which time the frames transform to their austenitic phase. The temperatures at which these transitions occur are affected by the nature of the alloy and the condition of the material.

In particular, nickel-titanium-based alloys (NiTi), wherein the transition temperature is slightly lower than body temperature, are preferred for the present invention. It can be desirable to have the transition temperature set at just below body temperature to insure a rapid transition from the martensitic state to the austenitic state when the frame can be implanted in a body lumen. For example, a nitinol frame can be deformed by collapsing the frame and creating stress which causes the NiTi to reversibly change to the martensitic phase. The frame can be restrained in the deformed condition inside a delivery sheath typically to facilitate the insertion into a patient's body, with such deformation causing the isothermal phase transformation. Once within the body lumen, the restraint on the frame can be removed, thereby reducing the stress thereon so that the superelastic frame returns towards its original undeformed shape through isothermal transformation back to the austenitic phase. The shape memory effect allows a nitinol structure to be deformed to facilitate its insertion into a body lumen or cavity, and then heated within the body so that the structure returns to its original, set shape.

The recovery or transition temperature may be altered by making minor variations in the composition of the metal and in processing the material. In developing the correct composition, biological temperature compatibility must be determined in order to select the correct transition temperature. In other words, when the frame can be heated, it must not be so hot that it can be incompatible with the surrounding body tissue. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

Alternatively, the tubular frame 20 can be designed to be expanded by mechanical means (i.e., the frames are not self-expanding). For example, the frame may be manufactured from an inert, biocompatible material with high corrosion resistance that can be plastically deformed at low-moderate stress levels, such as tantalum. The frames can be deployed by both assisted (mechanical) expansion and self-expansion means. In embodiments where the frame is deployed by mechanical expansion, the frame can be made from materials that can be plastically deformed. Other acceptable materials include stainless steel, titanium ASTM F63-83 Grade 1, niobium or high carat gold K 19-22. One widely used material for expandable structures is stainless steel, particularly 316L stainless steel. This material is particularly corrosion resistant with a low carbon content and additions of molybdenum and niobium. Fully annealed, stainless steel is easily deformable. Alternative materials for mechanically expandable structural frames that maintain similar characteristics to stainless steel include tantalum, platinum alloys, niobium alloys, and cobalt alloys.

In another embodiment, however, the medical device 10 may further include a means for translating the distal end 26 of the tubular frame 20 along the longitudinal axis 24 relative to the proximal end 28. This translation can move the tubular frame 20 from the compressed configuration to the expanded configuration. One embodiment may include a free standing distal end 26 and a fixed proximal end 28. The distal end 26 can be tied to a string, wire, or the like. The distal end 26 may then pulled by the string toward the proximal end 28, which can cause the members 32 to displace radially outward from the longitudinal axis 24. In another embodiment, the proximal end 28 may be free standing and the distal end 26 may be fixed. In this instance, a pusher sheath surrounding a catheter and adapted to engage the tubular medical device may be forced to translate distally the distal end 26, which may cause the members 32 to displace radially outward from the longitudinal axis 24. Yet, in another embodiment both proximal end 28 and distal end 26 may be free standing. Here, the string, as described above, may be pulled to urge the distal end 26 toward the proximal end 28, and the pusher sheath around the catheter, as described above, may urge the proximal end 28 toward the distal end 26. With both actions, the members 32 can be displaced radially outward from the longitudinal axis 24.

Optionally, the tubular frame 20 may be formed from or coated with other materials, such as polymers and bioabsorbable polymers may be included in or on the frame. The frame or portions thereof can optionally comprise material that permits identification of the position or orientation of the frame within a body passage. Radiopaque markers are advantageously positioned at one or more ends of the implantable frame to aid the physician in positioning the frame at a site inside a body vessel. For example, portions of the frame can include a radiopaque material that can be identified by X-rays. For example, U.S. Pat. No. 6,409,752, issued Jun. 25, 2002 to Boatman et al., incorporated herein by reference, discloses various radiopaque materials that can be used in or on the frame.

The tubular frame 20 may be fabricated using any suitable method known in the art. Preferably, the complete frame structure is cut from a solid tube, or cannula, or sheet of material, and thus the frame would be considered a monolithic unit. The cannula may have a circular, elliptical, or similar like cross-section. Laser cutting, water-jet cutting and photochemical etching are all methods that can be employed to form the structural frame from sheet and tube stock. A cannula may be provided having an outer surface and an interior surface that define a lumen about a longitudinal axis. The cannula, in addition, may have a proximal portion, a distal portion, and a middle region. A series of slots are cut between the distal portion and the proximal portion, or in the middle region of the cannula, and extend radially through the cannula from the outer surface to interior surface. The size of the slots, which indirectly affect the size of the members, can be substantially identical or can vary depending on if a region within in the body vessel needs more support or reinforcement. The slots may also be circumferentially spaced, substantially parallel, or both, from one another. Although the slots have typically a straight uniform circumferential width, the slots may be non-linear, such as sinusoidal, step-like, spiral or the like. The circumferential spacing can be equal between the slots. Still other methods for fabricating the complete frame structure as previously disclosed would be understood by one of ordinary skill in the art.

The tubular frame can be fabricated by using two smaller sized cannulas and a series of members, which are pre-cut. The two smaller cannulas can be a proximal cannula and a distal cannula, with each cannula having a proximal surface and a distal surface. The cross section of the series of members can be circular, elliptical, rectangular, or other, or any combination. Each member may have a proximal portion and a distal portion. The series of members can be attached in between two cannulas, i.e., between the distal surface of the proximal cannula and the proximal surface of the distal cannula. Moreover, the series of slots can be circumferentially spaced, substantially parallel, or both.

Other embodiments provide methods of making medical devices described herein. With reference to FIGS. 3 and 4A, one step of making may include cutting a series of slots 34 in the cannula to form the tubular frame 20. The series of slots 34 may be circumferentially spaced equal, substantially parallel, or both. If the cannula comprises a shape memory material, such as Nitinol, an inner mandrel with an outer diameter slightly less than the luminal diameter of the cannula is inserted into the lumen of the cannula. One end of the cannula can fixed or retained. One outer mold with a luminal diameter sized to match desired diameter of the body vessel 12 is inserted over the cannula. The unfixed end of the cannula is moved toward the retained end to urge the members 32 to move radially outward to contact the luminal surface of the outer mold. Once positioned, the unfixed end is then retained with the members 32 disposed radially outward.

Optionally, an insert mandrel can be sized to be inserted into the middle region 30 of the cannula. The insert mandrel is generally cylindrically shape, but can be any shape desired to align the contacting portion. The insert mandrel may also have two tapered portions to form the bend region between the contacting portion and the cannula. The two tapered portions may be conical. In this instance, the insert mandrel has an outer diameter to urge the members 32 to expand radially outward and to form the luminal surface of the members 32 when in the expanded configuration. The insert mandrel is sized to permit the contacting portion of the members to contact the body vessel wall. Between the outer mold and the insert mandrel, the contacting portion of the members 32 can conform therebetween to be substantially straight.

In another example, a pair of insert discs that are sized to urge the members 32 to expand radially outward and to form the luminal surface of the members 32 when in the expanded configuration. The insert discs disposed transversely can be moved axially away from each other along the inner mandrel. Each insert disc may have a tapered portion to form the bend region between the contacting portion and the cannula. Notwithstanding, the cannula with the outer mold and insert mandrel can be suitably heated, for example, 500 degrees C. and quenched to set the configuration and at a maximum radial force at 37 degrees C.

In other embodiments, the tubular frame can be constructed from sheet, wire (round or flat) or tubing. The method of fabrication can be selected by one skilled in the art depending on the raw material used. Techniques for forming implantable frames are discussed, for example, in Dougal et al., "Stent Design: Implications for Restenosis," Rev. Cardiovasc Med. 3 (suppl. 5), S16-S22 (2002), which is incorporated herein by reference in its entirety. In one embodiment using wires for the frame, one step of making the medical device may be to affix, solder, weld, or fuse the distal and proximal ends of a plurality of wires. Each wire may have a cross-sectional area geometry that is rectangular, triangular, circular, elliptical or the like. The wires can be conformed to a shape similar to what is described herein relative to the medical device. In one example, the wires comprise a shape memory alloy, such as Nitinol.

Another step may be applying the therapeutic agent 70 on the sleeve 60. Yet another step may include positioning the sleeve 60 around at least a portion of the middle region 130 of the tubular frame 20. Included in other embodiments is a step of contacting the sleeve 60 with the tubular frame 20 to form the medical device 10. The sleeve 60 may be maintained in contact with at least the portion of the plurality of members 132 in the compressed configuration and in the expanded configuration of the tubular frame 20.

The sleeve 60 may also include or be coated with the therapeutic agent 70, which can be any anti-restenosis drug, gene regulatory compound, anti-thrombotic, or other bioactive agents. The therapeutic agent 70 may include an anti-thrombogenic bioactive agent. The antithrombogenic bioactive agent may include any therapeutic agent that inhibits or prevents thrombus formation within a body vessel. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin. Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

In another aspect, the therapeutic agent 70 may be a fluid comprising an antisense therapeutic agent compound. The antisense compound may have: (i) morpholino subunits linked together by phosphorodiamidate linkages, 2 atoms long, joining the morpholino nitrogen of one subunit to the 5' exocyclic carbon of an adjacent subunit; and (ii) a sequence of bases attached to the subunits and containing a therapeutically beneficial antisense nucleotide sequence. While the compound need not necessarily 100% complementary to the target sequence, it is preferably effective to stably and specifically bind to the target sequence such that expression of the target sequence is modulated. The appropriate length of the oligomer to allow stable, effective binding combined with good specificity is about 8 to 40 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target is maintained. The compound preferably contains internal 3-base triplet complementary to the AUG site, and bases complementary to one or more bases 5' and 3' to the start site. One preferred compound sequence is the 20mer having the base sequence: 5'-ACG TTG AGG GGC ATC GTC GC-3', where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions. Preferably, the therapeutic agent 70 is a morpholino antisense compound having (i) from 8 to 40 nucleotides, including a targeting base sequence that is complementary to a region that spans the translational start codon of a c-myc mRNA; and (ii) uncharged, phosphorous-containing intersubunit linkages, in an amount effective to reduce the risk or severity of restenosis in the patient. These therapeutic agents are described in U.S. Pat. No. 7,094,765 and published U.S. patent application US 2006/0269587 A1, which are incorporated herein by reference in their entirety. While the therapeutic agent 70 is described with respect to certain preferred antisense compounds, any suitable therapeutic agent in fluid form (i.e., a gas and/or a liquid) or in a fluid carrier may be delivered from the multi-balloon catheter assembly.

Therapeutic agents 70 may be bonded to the sleeve 60 material, either directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to include a hydrophobic moiety such as a carbon based moiety, silicon-carbon based moiety or other such hydrophobic moiety. Alternatively, the hydrogen bonding interactions may be used to bind the bioactive agent to the coating layer.

Therapeutic agents 70 can be posited on the surface of the sleeve 60 material and a porous coating layer can be posited over the bioactive agent material. The sleeve 60 preferably includes at least one layer comprising a porous polyurethane material in contact with a second layer comprising a bioactive agent. The second layer can comprise a remodelable material or a biocompatible polyurethane, as well as a growth factor and/or a bioactive agent. Preferably, the inner surface of the sleeve 60 of the device comprises a porous polyurethane material over a layer comprising a suitable bioactive agent. The bioactive agent can diffuse through the porous polyurethane and into the body vessel, for example to locally deliver an antithrombogenic bioactive agent. A porous layer is preferably configured to permit diffusion of the bioactive agent from the medical device upon implantation within the body at a desirable elution rate. Prior to implantation in the body, the diffusion layer can be substantially free of the bioactive agent. Alternatively, the diffusion layer can comprise a bioactive agent within pores in the diffusion layer. The sleeve 60 can also be configured to release a bioactive from the outer surface of the device, by including a porous outer layer. Optionally, the porous layer can comprise a mixture of a biodegradable polymer and a bioactive positioned within pores of a biostable polymer of a diffusion layer. In another embodiment, the porous layer can comprise a mixture of a biodegradable polymer and a biostable polymer, configured to permit absorption of the biodegradable polymer upon implantation of the medical device to form one or more channels in the biostable polymer to permit an underlying bioactive agent to diffuse through the pores formed in the biostable polymer.

Application of the therapeutic agent 70 to the wall 17 of the body vessel 12 can occur by any means known in the art. The therapeutic agent 70 can be applied to the treatment site when the middle region 30 of the tubular frame 20 presses against the wall 17 of the body vessel 12. The therapeutic agent 70, however, can be applied based on the degradation of a coating on the drug at sometime after the sleeve 60 of the tubular frame 20 presses against the wall 17 of the body vessel 12.

Depending on the condition of the patient or subject, the drug applied will be specific for such condition, i.e., the concentration, potency, or both, may be limited to only to the immediate site of treatment, to other areas surrounding the site of treatment, or both. Different therapeutic agents can be applied to the portion of the sleeve 60 contacting the body vessel wall 17 to promote blood clotting or other therapy between the sleeve 60 and the body vessel wall 17. While other therapeutic agents can be applied to the portion of the sleeve 60 not in contact with the body vessel wall, including the tubular frame, to prevent blood clotting or other therapy within the lumen 22' of the medical device 10.

The therapeutic agent 70 can be delivered to the treatment site in several ways with the medical device 10, as described herein. In one non-limiting example, the medical device 10 is self-expanding and may be radially compressed and inserted into the sheath 9. The system 8 with the catheter 9 and the medical device 10, as shown in FIG. 1, can be inserted into the body and traversed through the body vessel 12 to the treatment site. The medical device 10 may be deployed at such point to bring the sleeve 60 in contact with the body vessel 12. Deployment can be accomplished by translating the sheath 9 in the proximal direction to permit the middle region 30 of the tubular frame 20 to radially expand from the compressed configuration to the expanded configuration, as shown in FIG. 2A. After deployment, the medical device 10 and sleeve 60 can be maintained in contact with the wall 17 of the body vessel 12. The therapeutic agent 70 may be then delivered at the point of treatment within the body vessel 12.

There are many factors to determine the duration of the deployment step to deliver the therapeutic agent 70, such as the condition and its severity on the subject, the type of treatment, the type of therapeutic agent 70, etc. Once the procedure is completed, the medical device 10 can then be radially compressed from the expanded configuration to the compressed configuration to withdraw the sleeve 60 from contact with the wall 17 of the body vessel 12. The sheath 9 can be translated to the distal direction to urge the medical device 10 to the compressed configuration. The medical device 10 can be removed from the point of treatment and withdrawn from the body vessel 12. As appreciated by one ordinary skilled in the art, the medical device 10 may not be self-expanding, and can be delivered using the methods described herein to impart mechanical expansion of the device. As appreciated by one ordinary skilled in the art, the system 8 can be maintained in the body vessel for a suitable duration of time to deliver the therapeutic agent, or the delivery system can be removed and the medical device 10 may left implanted within the body vessel for a longer period and later removed through an independent procedure. The implanted medical device can be retrieved by means known by one ordinary skilled in the art.

The medical device 10 can also be an alternative therapy to apply hemostasis and/or remodeling to the lacerated hole 12A of the body vessel 12. Vascular wounds, defects, or punctures, especially in a larger artery can be life threatening, causing massive hemorrhaging. Therefore, the vascular wound must be closed to prevent massive hemorrhage and to promote hemostasis. Patients undergoing procedures can be treated with anti-coagulants such as heparin, thrombolytics, and the like. The medical device 10 can promote the use the body's own natural mechanism to achieve hemostasis by providing hemostasis by sealing the lacerated hole 12A from the inside of the body vessel wall 17. The medical device 10 can be left in place at the treatment site of the body vessel wall until hemostasis is reached and thereafter removed. Removal of the medical device 10 can occur in order for there to be minimal disruption of the coagulant that is formed at the lacerated hole 12A. If there is residual bleeding after removal, the user may apply a few minutes of external manual pressure at the lacerated hole 12A after the removal of the device to achieve complete hemostasis. The sleeve 60 of the medical device 10 may also include the therapeutic agent 70, such as highly thrombogenic substances, which can also be, in addition to application to the sleeve 60, mixed and injected at the lacerated hole 12A for the purpose of accelerating the hemostatic process. These therapeutic agents 70 can contain one or more clot promoting substances, such as thrombin and/or fibrinogen, along with other substances, such as collagen. In addition, the sleeve 60 can comprise a remodelable material, as described above.

The medical device 10 can be a tamponade for a lacerated body vessel and can be applied to the body vessel wall 17 to occlude the lacerated hole 12A from inside the body vessel wall 17. The medical device 10 is inserted through the body vessel 12 in the delivery compressed configuration, and delivered to the treatment site and/or the lacerated hole 12A. The medical device 10 is radially expanded urging the sleeve 60 against the body vessel wall 17. With the sleeve 60 pressed against the body vessel wall 17, the one or more clot promoting substances of the therapeutic agents applied to the sleeve 60, or the sleeve itself, can adequately be permitted to contact the body vessel wall 17. The portion of the sleeve 60 contacting the body vessel wall 17 may include pro-coagulants to promote blood clotting between the sleeve and the body vessel wall. The portion of the sleeve 60 not in contact with the body vessel wall, including the tubular frame, may include anti-coagulants to prevent blood clotting within the lumen of the medical device. The medical device 10 may then be removed. Preferably, the sleeve 60 comprises a foamed extracellular matrix and is sized to at least cover the lacerated hole. A therapeutic agent, described herein, can be applied on the foamed ECM sleeve to seal the sleeve against the wall of the body vessel, to promote faster hemostasis, to promote remodeling or cell growth, and/or to promote regrowth and healing of damaged or diseased body vessel.

It is therefore intended that the foregoing detailed description be regarded as illustrative rather than limiting, and that it be understood that it is the following claims, including all equivalents, that are intended to define the spirit and scope of this invention.

The invention claimed is:

1. A method of applying vascular therapy to a wall of a body vessel, the method comprising:
   introducing a medical device attached to a distal end of a catheter in a compressed configuration into a body vessel and traversing through the body vessel to a point of treatment, the medical device comprising a tubular frame defining a lumen about a longitudinal axis, the tubular frame having a distal end, a proximal end, and a middle region therebetween, the middle region of the tubular frame including a plurality of members with slots therebetween, where the middle region of the tubular frame is moveable from a compressed configuration to an expanded configuration, where in the compressed configuration the members lie in immediate contiguous proximity to each other, and in the expanded configuration each of the members comprises two bends and a contacting portion therebetween, the contacting portion displaced radially outward from the longitudinal axis to form interstices between adjacent members, and a sleeve encompassing a portion of only the contacting portion of the members of the middle region of the tubular frame,
   radially expanding the members of the middle region of the tubular frame from the compressed configuration to the expanded configuration so that the contacting portion of the members is placed in close proximity to the body vessel wall and the sleeve is urged to contact the wall of said body vessel; and
   maintaining the sleeve in contact with the wall of said body vessel to apply vascular therapy at the point of treatment within the body vessel, where the point of treatment comprises a lacerated hole extending laterally through the entire wall of said body vessel, the sleeve covering the entire lacerated hole to promote hemostasis when the sleeve is in contact with the wall of said body vessel, while the interstices permit fluid flow to areas distal to the point of treatment, the catheter remaining attached to said medical device while the fluid flows through the interstices.

2. The method of claim 1, where in the expanded configuration the contacting portion is configured to substantially align with said body vessel wall.

3. The method of claim 1, where at least the middle region of the tubular frame is self-expanding.

4. The method of claim 1, where the medical device further comprises a therapeutic agent disposed on the sleeve, where the therapeutic agent is configured to be delivered when the sleeve is in contact with the wall of said body vessel.

5. The method of claim 1, where the middle region of the tubular frame has a first diameter in the compressed configuration and the contacting portion of the middle region has a second diameter in the expanded configuration that is greater than the first diameter, where the first diameter is substantially identical to the diameter of at least one of the proximal and distal ends of the tubular frame in the compressed configuration.

6. The method of claim 5, where the second diameter is greater than the diameter of at least one of the proximal and distal ends of the tubular frame in the expanded configuration.

7. The method of claim 1, where the sleeve further comprises a remodelable material.

8. The method of claim 7, where the remodelable material comprises a foamed extracellular matrix.

9. The method of claim 1, where the sleeve material further comprises a therapeutic agent.

10. A method of preventing fluid flow through an opening formed in a wall of a body vessel, while maintaining fluid perfusion to areas beyond the opening, the method comprising:
   delivering a perfusion medical device attached to a distal end of a catheter in a compressed configuration to a treatment site to cover said opening in the body vessel wall from inside the vessel, the device comprising a tubular frame defining a lumen about a longitudinal axis, the tubular frame having a distal end, a proximal end, and a middle region therebetween, the middle region of the tubular frame including a contacting portion circumferentially spaced about the longitudinal axis, the device being radially expandable from the compressed configuration to an expanded configuration, where, in the compressed configuration, said contacting portion is spaced from the longitudinal axis at about the same diameter of the ends, and where, in the expanded configuration, said contacting portion is displaced radially outward from the longitudinal axis at a greater diameter than the diameter of at least one of the proximal and distal ends to form interstices therebetween, and a therapeutic sleeve encompassing said contacting portion, the therapeutic sleeve having a first configuration when the device is in the compressed configuration and a second configuration when the device is in the expanded configuration;

expanding the device to the expanded configuration so that the therapeutic sleeve is in the second configuration and entirely covers said opening in the body vessel wall, said opening extending laterally through the entire wall of the body vessel; and maintaining contact between the therapeutic sleeve and the body vessel wall to cover said opening in the body vessel wall for a pre-determined period of implantation, while the interstices formed by said contacting portion permit fluid flow to areas away from the treatment site, the catheter remaining attached to said medical device while the fluid flows through the interstices.

11. The method of claim 10, where the therapeutic sleeve further comprises a remodelable material.

12. The method of claim 11, where the remodelable material further comprises a foamed extracellular matrix.

13. The method of claim 11, where the therapeutic sleeve further comprises a therapeutic agent.

14. The method of claim 10, further comprising injecting a therapeutic agent at said opening in the body vessel wall.

15. A method of applying therapy to a wall of a body vessel with a medical device, while maintaining fluid perfusion distal to the medical device, the method comprising:

introducing a system within a body vessel, the system comprising a catheter attached to a perfusion medical device in a compressed configuration disposed at a distal end of the catheter, the medical device comprising a tubular frame defining a lumen about a longitudinal axis, the tubular frame having a distal end, a proximal end, and a middle region therebetween, the middle region of the tubular frame including a contacting portion circumferentially spaced about the longitudinal axis, the contacting portion being radially self-expandable from a compressed configuration to an expanded configuration, where, in the compressed configuration, the middle region and the proximal and distal ends of the tubular frame are spaced from the longitudinal axis at about a first diameter, and where, in the expanded configuration, the contacting portion is displaced radially outward from the longitudinal axis to a second diameter, where each member comprises an angled portion connected between the proximal end of the tubular frame and the contacting portion to form interstices between each of the angled portions, where the second diameter is greater than the first diameter of at least one of the proximal and distal ends of the tubular frame, and a sleeve encompassing only the contacting portion, the sleeve having a first configuration when the contacting portion is in the compressed configuration and a second configuration when the contacting portion is in the expanded configuration;

positioning the system within the body vessel so that the perfusion medical device is at a treatment site;

expanding the contacting portion of the perfusion medical device to the expanded configuration so that the sleeve is in the second configuration and contacts the body vessel wall; and maintaining contact between the sleeve and the body vessel wall for a predetermined period of implantation, where the treatment site comprises a lacerated hole extending laterally through the entire wall of said body vessel, the sleeve covering the entire lacerated hole to promote hemostasis when the sleeve is in contact with the wall of said body vessel, while the interstices formed by the members permit fluid flow to areas away from the treatment site, the catheter remaining attached to said medical device while the fluid flows through the interstices.

16. The method of claim 15, where the system further comprises a sheath disposed around the catheter, the sheath positionable around the perfusion medical device to maintain the perfusion medical device in the compressed configuration during the introducing and positioning steps, where the sheath is slidably removed from the perfusion medical device during the expanding step.

17. The method of claim 16, further comprising the step of re-compressing the contacting portion of the perfusion medical device to the compressed configuration by sliding the sheath over the perfusion medical device at the treatment site after the maintaining step.

18. The method of claim 15, where the therapeutic sleeve further comprises a therapeutic agent.

* * * * *